United States Patent
Lin et al.

(10) Patent No.: US 6,664,280 B2
(45) Date of Patent: Dec. 16, 2003

(54) ANTIVESICANT COMPOUNDS AND METHODS OF MAKING AND USING THEREOF

(75) Inventors: Ai J. Lin, North Potomac, MD (US); Michael C. Babin, Bel Air, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 10/172,074

(22) Filed: Jun. 17, 2002

(65) Prior Publication Data

US 2003/0055090 A1 Mar. 20, 2003

Related U.S. Application Data

(62) Division of application No. 09/911,520, filed on Jul. 25, 2001.

(51) Int. Cl.[7] .................. A61K 31/44; C07D 213/70

(52) U.S. Cl. ........................ 514/358; 546/347

(58) Field of Search .................... 546/347; 514/358

(56) References Cited

U.S. PATENT DOCUMENTS

| | | | |
|---|---|---|---|
| 2,649,389 A | 8/1953 | Williams | |
| 3,700,676 A | 10/1972 | Damico | 260/294.8 |
| 3,773,770 A | 11/1973 | Damico | 260/290 |
| 3,892,760 A | 7/1975 | Hooks, Jr. et al. | 260/294.8 |
| 3,954,781 A | 5/1976 | Hooks, Jr. et al. | 260/294.8 |

OTHER PUBLICATIONS

2–mercaptopyridine–N–oxide . . . Ai J. Lin 1998.*
2–Mercaptopyridine–N–oxides and 2–mercaptoquinoline–N–oxides as potential catalytic deactivators of mustards by Lin Ai L . Caplus 128:253888 English Abstract.*
Auerbach, et al., "Chemical Production of Mutations", Abstract, Nature 157 (1946).
Bronaugh, et al., "Methods for in Vitro Percutaneous Absorption Studies II. Animal Models for Human Skin", Toxicology and Applied Pharmacology. 62:481–488 (1982).
Clayson, et al., "Effect of Poly (ADP–Ribose) Polymerase inhibitors on Sulfur Mustard (HD)–Induced Cell Death", Med. Defense Biosci. Rev., pp. 127–130, (1991).
Cowan, et al., "Inhibition of Sulfur Mustard–increased Protease Activity By Niacinamide, N–Acetyl–L–Cysteine or Dexamethasone", Proceed. 1991 Med. Defense Biosci. Rev., pp. 155–158, (1991).
Cullumbine, "Medical Aspects of Mustard Gas Poisoning", Nature. 159:151–153 (1947).
Dannenberg, et al., Extracellular Collagenase, Proteoglycanase and Serum Proteinase Inhibitors in Developing and Healing Sulfur Mustard Lesions, Proceed. 1991 Med. Defense Biosci. Rev., pp. 147–150, (1991).

Drasch, et al., "Concentrations of Mustard Gas [Bis(2–Chloroethyl)Sulfide] in the Tissues of a Victim of a Vesicant Exposure", J. of Forensic Sciences JESCA. 32(6):1788–1793 (1987).
Furukawa et al., "Sytheses of Pyridine Derivatives. IX. Preparation of Pyridinealdehydes. 2. Preparation of Several Derivatives of 2– or 4–Pyridinealdehyde 1–oxides", Chemical Abstracts, 53:1958.
Gross et al., "Sulfur Mustard Lowers Nicotiramice Adenine Dinucleotide Concentrations in Human Skin Grafted to Athymic Nude Mice", Toxicology and Applied Pharmacology. 81: 85–90 (1985).
Hamana et al., "The Reaction of Quinoline N–Oxide With N,N–Diethylthiocarbamoyl Chloride", pp. 241–245 (1973).
Heston et al., "Carcinogenic Action of the Mustards", Journal National Cancer Institute, vol. 11: pp. 415–423 (1950).
Katritzky, "The Preparation of Some Substituted Pyridine 1–Oxides", pp. 2404–2408 (1955).
Meier, "The Time Dependent Effect of 2.2'–Dichlorodiethyl Sulfide (Sulfur Mustard, HD) on Lymphocyte Viability and the Time Course for Protection by Poly (ADP–Ribose) Polymerase Inhibitors", Proceed. 1991 Med. Defense Biosci. Rev., pp. 135–138 (1991).
Ochiai, "Recent Japanese Work on the Chemistry of Pyridine 1–Oxide and Related Compounds", Bunnett, University of North Carolina, Chapel Hill. 18:534–551 (1953).
Ogston et al., "The Replacement Reactions of β–β'–Dichlorodiethyl Sulphide and of Some Analogues in Aqueous Solution: The Isolation of β–Chloro–β'–Hydroxy Diethyl sulphide", Trans. Fara. Soc. 44:45–52 (1948).
Powers, et al., "Protease Inhibitors as Antivesicants", Proceed. 1991 Med. Defense Biosci. Rev., pp. 41–48 (1991).
Papirmeister et al., "Pathology Produced by Sulfur Mustard in Human Skin Grafts on Athymic Nude Mice. II. Ultrastructural Changes", J. Toxicol.–Cut. & Ocular Toxicol. 3(4): 393–408 (1984).

(List continued on next page.)

*Primary Examiner*—Rita Desai
(74) *Attorney, Agent, or Firm*—Elizabeth Arwine

(57) ABSTRACT

As disclosed herein, the present invention provides a compound having the structural formula

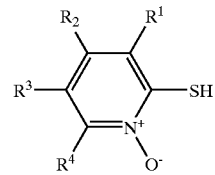

wherein $R^1$, $R^2$, $R^3$, and $R^4$ are each independently H, or a methyl, halo, trifluoromethyl, nitro, alkyloxy, or acyloxy group, or a pharmaceutically acceptable salt or prodrug thereof. Also disclosed are compounds, compositions, methods and kits for treating, preventing, or inhibiting injuries induced by a vesicant agent, such as bis-2-chloroethylsulfide (HD). Additionally, protectants and decontaminants are disclosed.

9 Claims, No Drawings

OTHER PUBLICATIONS

Papirmeister, et al., "Molecular Basis for Mustard–Induced Vesication", Fundam. Appl. Toxicol. 5: S134–148 (1985).

Papirmeister, et al., "Pathology Produced by Sulfur Mustard in Human Skin Grafts on Athymic Nude Mice. I. Gross and Light Microscopic Changes", J. Toxicol.–Cut. & Ocular Toxicol. 3(4):371–391 (1984).

Purnell et al., "Novel Inhibitors of Poly(ADP–Ribose) Synthetase", Biochem. J. 185:775–777 (1980).

Quayle et al., "A Kinetic Study of the Reactions of n–Butyl Bromide with the Sodium Salts of Phenol, Thiophenol and n–Butyl Mercaptan", J. Amer. Chem. Soc. 64:226–230 (1942).

Rankin et al., "Quantitative Studies of Inhibitors of ADP–Ribosylation in Vitro and in Vivo", The Journal of Biological Chemistry. 264(8):4312–4317 (1989).

Sestili, et al., "Analysis of Benzamide as Poly (ADP–Ribose) Transferase Inhibitors: Study on Structure Activity Relationships", Pharmacological Research Communications. 20(7):613–614 (1988).

Vojvodic, et al., "The Protective Effect of Different Drugs in Rats Poisoned by Sulfur and Nitrogen Mustards", Fundam. Appl. Toxicol, pp. S160–168 (1985).

Walker, et al., "Protection of L–Cells by Thoils Against the Toxicity of Sulfur Mustard", Canadian Journal of Physiology and Pharmacology. 47(2):143–151 (1969).

Wheeler, "Studies Related to the Mechanisms of Action of Cytotoxic Alkylating Agents: A Review", Cancer Research. 22(6):651–688 (1962).

* cited by examiner

ANTIVESICANT COMPOUNDS AND METHODS OF MAKING AND USING THEREOF

CROSS REFERENCE TO RELATED APPLICATIONS

This application is a divisional of U.S. Utility application Ser. No. 09/911,520, filed Jul. 25, 2001, naming Ai J. Lin and Michael C. Babin as joint inventors, which is herein incorporated by reference in its entirety.

ACKNOWLEDGMENT OF GOVERNMENT SUPPORT

This invention was made by employees of the United States Army. The government has rights in the invention.

BACKGROUND OF THE INVENTION

1. Field of the Invention

This invention relates generally to antivesicant compounds and methods of making and using thereof. In particular, the present invention relates to antivesicant compounds comprising 2-mercaptopyridine-N-oxide as a backbone structure.

2. Description of the Related Art

Vesicants are chemical warfare agents which cause blisters and include sulfur mustard, nitrogen mustard, Lewisite, and phosgene oxime. Bis-2-chloroethylsulfide (HD) is a radiomimetic alkylating agent that has mutagenic, cytotoxic, and carcinogenic properties. See Auerbach, C, et al. (1946) Nature 157:302; Wheller, G. P. (1962) Cancer Res. 22:651–688; and Heston, W. E. (1950) J. Natl. Cancer. Inst. 11:415–423. In the battlefield, HD has been used as a chemical weapon which produces incapacitating blistering injuries at the site of exposure. See Collumbine, H. (1947) Nature 159:151–153; Papirmeister, B., et al. (1984) J. Cut. and Ocular Toxicol. 3:371–393; and Vogt, R. F. et al. (1984) Fundam. Appl. Toxicol. 4(2):571–583.

Biochemical studies on cells exposed to HD indicate that DNA alkylation is the primary lesion which leads to a series of biochemical changes, including depurination of DNA strands, DNA break, activation of chromosomal enzyme poly(ADP-ribose)polymerase, depletion of cofactor $NAD^+$, inhibition of glycolysis, elevation of protease activity and finally blister formation. See Papirmeister, B., et al. (1985) Fundam. Appl. Toxicol. 5:S134. Chemically, HD first forms a reactive sulfonium intermediate which then reacts randomly with macromolecules, such as DNA, RNA and protein. See Walker, I. G., et al. (1969) Canadian J. Physiol. Pharmacol. 47(2):143–151; and Ogston, A. G., et al. (1948) Trans. Fara. Soc. 44:45. The alkylation of DNA is what causes the drastic biochemical changes and blister formation. The site of alkylation on DNA is found to be the $N^7$ of purine bases, particularly guanidine.

Various approaches have been attempted in order to find therapeutic compounds which prevent blister formation caused by HD exposure. For example, the examination of poly(ADP-ribose)polymerase or protease as potential target enzymes have been emphasized in recent years. See Purnell, M. R., et al. (1980) Biochem. J. 185:775; Sestili, P., et al. (1988) Pharm. Res. Comm. 20:613; Rankin, P. W., et al. (1989) J. Biol. Chem. 264:4312; Powers, J. C., et al. (1991) Proceed. 1991 Med. Defense Biosci. Rev. 41–48; and Cowan, F. M., et al. (1991) Proceed. 1991 Med. Defense Biosci. Rev. 155–158. Inhibitors of these two enzymes have been shown to decrease the toxicity of HD. See Clayson, E. T., et al. (1991) Proceed. 1991 Med. Defense Biosci. Rev. 127–130; Meiers, H. L. Proceed. 1991 Med. Defense Biosci. Rev. 135–142; and Dannenberg, Jr., A. M. et al. (1991) Proceed. 1991 Med. Defense Biosci. Rev. 147–150.

Other approaches are based on compounds which possess strong nucleophilicity and react rapidly with HD to produce non-invasive products. See Ogston, A. G., et al. (1948) Trans. Fara. Soc. 44:45. For example, sulfur containing chemicals, such as cysteine, glutathione and 2-mercaptoethylamines have been shown to protect cells from HD toxicity in experimental animals. See Walker, I. G., et al. (1969) Canadian J. Physiol. Pharmacol. 47(2):143–51. These mercapto compounds protect the cell by interacting with HD to form non-reactive sulfides. The practical values of the above mentioned sulfur compounds, however, are impaired by either poor passage of the drugs across the cell membrane, easy oxidation to form inactive disulfide or their poor nucleophilicity. It has been shown that sulfide anions ($RS^-$) are much stronger nucleophiles than the free thiols (RSH). See Reid, E. E.: ORGANIC CHEMISTRY OF BIVALENT SULFUR, Vol. II. Chapt. 5, 237–288, Chemical Publishing Co., Inc., New York, N.Y. (1960); and Quayle, O. R. et al. (1942) J. Amer. Chem. Soc. 64:226–230. For example, sodium thiophenol (PhSNa) reacts with n-butylbromide one thousand times faster than thiophenol (PhSH). Since the aliphatic thiols, such as cysteine and glutathione, do not ionize in physiological pH, their nucleophilicity are weak under physiological conditions and thus have limited potential as a scavenger of HD.

Despite all the research and various approaches, the biochemical mechanism of HD-induced injury is still not fully understood and no effective treatment for HD-induced injury is available. Thus, a need still exists for effective treatments for HD-induced injuries.

SUMMARY OF THE INVENTION

The present invention generally relates to a compound having the structural formula

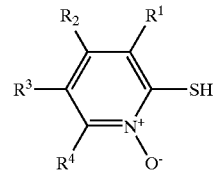

wherein $R^1$, $R^2$, $R^3$, and $R^4$ are each independently H, or a methyl, halo, trifluoromethyl, nitro, alkyloxy, or acyloxy group, or a pharmaceutically acceptable salt or prodrug thereof. In some embodiments, two adjacent R substituents may form a cycloalkyl, heterocycloalkyl, aryl, or heteroaryl group. In some preferred embodiments, $R^1$, $R^2$, $R^3$ and $R^4$ are each independently H, methyl, methoxy, chloro, fluoro, or bromo. In some preferred embodiments, the compound is 2-mercaptopyridine-N-oxide, 4-methyl-2-mercaptopyridine-N-oxide, 6-methyl-2-mercaptopyridine-N-oxide, 4,6-dimethyl-2-mercaptopyridine-N-oxide, 5-bromo-2-mercaptopyridine-N-oxide, 5-methyl-2-mercaptopyridine-N-oxide, 3-chloro-2-mercaptopyridine-N-oxide, 5-chloro-2-mercaptopyridine-N-oxide, 4-chloro-2-mercaptopyridine-N-oxide, 3,4,5, or 6-methoxy-2-mercaptopyridine-N-oxide, 5-trifluoromethyl-2-mercaptopyridine-N-oxide, 2-mercaptoquinoline-N-oxide, or a pharmaceutically acceptable salt or prodrug thereof. In some embodiments, the compound is an antivesicant.

In some embodiments, the present invention provides a pharmaceutical composition comprising a compound having the structural formula

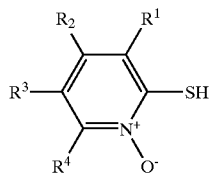

wherein $R^1$, $R^2$, $R^3$, and $R^4$ are each independently H, or a methyl, halo, trifluoromethyl, nitro, alkyloxy, or acyloxy group, or a pharmaceutically acceptable salt or prodrug thereof, and a pharmaceutically acceptable excipient. In some embodiments, two adjacent R substituents may form a cycloalkyl, heterocycloalkyl, aryl, or heteroaryl group. In some preferred embodiments, $R^1$, $R^2$, $R^3$, and $R^4$ are each independently H, methyl, methoxy, chloro, fluoro, or bromo. In some embodiments, the compound is 2-mercaptopyridine-N-oxide, 4-methyl-2-mercaptopyridine-N-oxide, 6-methyl-2-mercaptopyridine-N-oxide, 4,6-dimethyl-2-mercaptopyridine-N-oxide, 5-bromo-2-mercaptopyridine-N-oxide, 5-methyl-2-mercaptopyridine-N-oxide, 3-chloro-2-mercaptopyridine-N-oxide, 5-chloro-2-mercaptopyridine-N-oxide, 4-chloro-2-mercaptopyridine-N-oxide, 3,4,5, or 6-methoxy-2-mercaptopyridine-N-oxide, 5-trifluoromethyl-2-mercaptopyridine-N-oxide, 2-mercaptoquinoline-N-oxide, or a pharmaceutically acceptable salt or prodrug thereof. In some embodiments, the pharmaceutical composition further comprises a second antivesicant compound. In some embodiments, the pharmaceutical composition further comprises a supplementary active compound such as an anti-inflammatory or an anti-protease drug or compounds.

In some embodiments, the present invention is directed to protectant or decontaminant comprising a compound having the structural formula

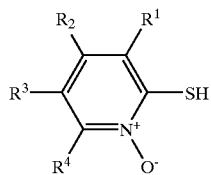

wherein $R^1$, $R^2$, $R^3$, and $R^4$ are each independently H, or a methyl, halo, trifluoromethyl, nitro, alkyloxy, or acyloxy group. In some embodiments, two adjacent R substituents of the compound form a cycloalkyl, heterocycloalkyl, aryl, or heteroaryl group. In preferred embodiments, $R^1$, $R^2$, $R^3$, and $R^4$ are each independently H, methyl, methoxy, chloro, fluoro, or bromo. In some preferred embodiments, the compound is 2-mercaptopyridine-N-oxide, 4-methyl-2-mercaptopyridine-N-oxide, 6-methyl-2-mercaptopyridine-N-oxide, 4,6-dimethyl-2-mercaptopyridine-N-oxide, 5-bromo-2-mercaptopyridine-N-oxide, 5-methyl-2-mercaptopyridine-N-oxide, 3-chloro-2-mercaptopyridine-N-oxide, 5-chloro-2-mercaptopyridine-N-oxide, 4-chloro-2-mercaptopyridine-N-oxide, 3,4,5, or 6-methoxy-2-mercaptopyridine-N-oxide, 5-trifluoromethyl-2-mercaptopyridine-N-oxide, or 2-mercaptoquinoline-N-oxide. The protectant or decontaminant may be clothing, combat gear, a protective shelter, a weapon, a piece of equipment, a filter, a sponge, a foam, a spray, a lotion, or a gas. The protectant or decontaminant may be used to prevent exposure of a subject to a vesicant agent. The protectant may be used to treat a subject exposed to a vesicant agent or treat an injury induced by a vesicant agent. The decontaminant may be used to decontaminate a subject or an object exposed to a vesicant agent. In some embodiments, the protectant or decontaminant further comprises a second antivesicant compound, a supplementary active compound, or both. In some embodiments, the present invention provides a kit comprising the protectant or decontaminant and instructions for use.

In some embodiments, the present invention provides a method of treating, preventing, or inhibiting an injury induced by a vesicant agent comprising administering at least one compound having the structural formula

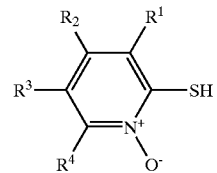

wherein $R^1$, $R^2$, $R^3$, and $R^4$ are each independently H, or a methyl, halo, trifluoromethyl, nitro, alkyloxy, or acyloxy group, or a pharmaceutically acceptable salt or prodrug thereof to a subject. Two adjacent R substituents may form a cycloalkyl, heterocycloalkyl, aryl, or heteroaryl group. In some preferred embodiments, $R^1$, $R^2$, $R^3$, and $R^4$ are each independently H, methyl, methoxy, chloro, fluoro, or bromo. In some embodiments, the compound is 2-mercaptopyridine-N-oxide, 4-methyl-2-mercaptopyridine-N-oxide, 6-methyl-2-mercaptopyridine-N-oxide, 4,6-dimethyl-2-mercaptopyridine-N-oxide, 5-bromo-2-mercaptopyridine-N-oxide, 5-methyl-2-mercaptopyridine-N-oxide, 3-chloro-2-mercaptopyridine-N-oxide, 5-chloro-2-mercaptopyridine-N-oxide, 4-chloro-2-mercaptopyridine-N-oxide, 3,4,5, or 6-methoxy-2-mercaptopyridine-N-oxide, 5-trifluoromethyl-2-mercaptopyridine-N-oxide, 2-mercaptoquinoline-N-oxide, or a pharmaceutically acceptable salt or prodrug thereof. In some embodiments, the injury is an HD-induced injury. The compound may be administered before, during, after, or a combination thereof exposure to the vesicant agent. In some embodiments, the method includes administering a second antivesicant compound, a supplementary active compound, or both to the subject before, during, after or a combination thereof exposure to the vesicant agent. The compound may be administered topically or systemically.

In some embodiments, the present invention relates to a method of decontaminating an area exposed to a vesicant agent comprising contacting a compound having the structural formula

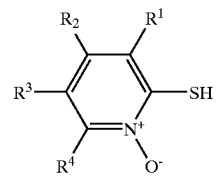

wherein $R^1$, $R^2$, $R^3$, and $R^4$ are each independently H, or a methyl, halo, trifluoromethyl, nitro, alkyloxy, or acyloxy group with the area. Two adjacent R substituents may form a cycloalkyl, heterocycloalkyl, aryl, or heteroaryl group. In some preferred embodiments, $R^1$, $R^2$, $R^3$, and $R^4$ are each independently H, methyl, methoxy, chloro, fluoro, or bromo. In some embodiments, the compound is 2-mercaptopyridine-N-oxide, 4-methyl-2-mercaptopyridine-N-oxide, 6-methyl-2-mercaptopyridine-N-oxide, 4,6-dimethyl-2-mercaptopyridine-N-oxide, 5-bromo-2-mercaptopyridine-N-oxide, 5-methyl-2-mercaptopyridine-N-oxide, 3-chloro-2-mercaptopyridine-N-oxide, 5-chloro-2-mercaptopyridine-N-oxide, 4-chloro-2- mercaptopyridine-N-oxide, 3,4,5, or 6-methoxy-2-mercaptopyridine-N-oxide, 5-trifluoromethyl-2-mercaptopyridine-N-oxide, or 2-mercaptoquinoline-N-oxide. In some embodiments, the vesicant agent comprises HD. In some embodiments, a second antivesicant compound, a supplementary active compound, or both may be applied to the area exposed to the vesicant agent.

In some embodiments, the present invention provides a kit for treating, preventing, or inhibiting an injury induced by a vesicant agent comprising at least one compound having the structural formula

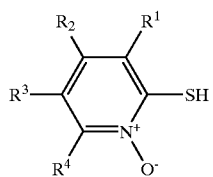

wherein $R^1$, $R^2$, $R^3$, and $R^4$ are each independently H, or a methyl, halo, trifluoromethyl, nitro, alkyloxy, or acyloxy group, or a pharmaceutically acceptable salt or prodrug thereof and instructions for use. In some embodiments, two adjacent R substituents of the compound may form a cycloalkyl, heterocycloalkyl, aryl, or heteroaryl group. In some preferred embodiments, $R^1$, $R^2$, $R^3$, and $R^4$ are each independently H, methyl, methoxy, chloro, fluoro, or bromo. In some embodiments, the compound is 2-mercaptopyridine-N-oxide, 4-methyl-2-mercaptopyridine-N-oxide, 6-methyl-2-mercaptopyridine-N-oxide, 4,6-dimethyl-2-mercaptopyridine-N-oxide, 5-bromo-2-mercaptopyridine-N-oxide, 5-methyl-2-mercaptopyridine-N-oxide, 3-chloro-2-mercaptopyridine-N-oxide, 5-chloro-2-mercaptopyridine-N-oxide, 4-chloro-2-mercaptopyridine-N-oxide, 3,4,5, or 6-methoxy-2-mercaptopyridine-N-oxide, 5-trifluoromethyl-2-mercaptopyridine-N-oxide, 2-mercaptoquinoline-N-oxide, or a pharmaceutically acceptable salt or prodrug thereof. In some embodiments, the kit further comprises a second antivesicant compound. In some embodiments, the kit further comprises a supplementary active compound such as an anti-inflammatory or an anti-protease drug or compound.

In some embodiments, the present invention is directed to a kit for decontaminating an area exposed to a vesicant agent comprising at least one compound having the structural formula

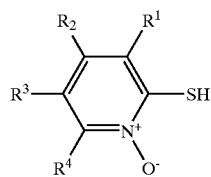

wherein $R^1$, $R^2$, $R^3$, and $R^4$ are each independently H, or a methyl, halo, trifluoromethyl, nitro, alkyloxy, or acyloxy group and instructions for use. In some embodiments, two adjacent R substituents of the compound may form a cycloalkyl, heterocycloalkyl, aryl, or heteroaryl group. In some preferred embodiments, $R^1$, $R^2$, $R^3$, and $R^4$ are each independently H, methyl, methoxy, chloro, fluoro, or bromo. In some embodiments, the compound is 2-mercaptopyridine-N-oxide, 4-methyl-2-mercaptopyridine-N-oxide, 6-methyl-2-mercaptopyridine-N-oxide, 4,6-dimethyl-2-mercaptopyridine-N-oxide, 5-bromo-2-mercaptopyridine-N-oxide, 5-methyl-2-mercaptopyridine-N-oxide, 3-chloro-2-mercaptopyridine-N-oxide, 5-chloro-2-mercaptopyridine-N-oxide, 4-chloro-2-mercaptopyridine-N-oxide, 3,4,5, or 6-methoxy-2-mercaptopyridine-N-oxide, 5-trifluoromethyl-2-mercaptopyridine-N-oxide, or 2-mercaptoquinoline-N-oxide. In some embodiments, the kit further comprises a second antivesicant compound.

It is to be understood that both the general description and the detailed description herein are exemplary only and are intended to illustrate several embodiments of the invention, explain the principles of the invention, and provide further explanation of the invention as claimed.

DETAILED DESCRIPTION OF THE INVENTION

Generally, the present invention provides 2-mercaptopyridine-N-oxide compounds for treating, preventing, or inhibiting injuries induced by vesicant agents which includes sulfur mustard (bis-2-chloroethylsulfide (HD)), Nitrogen mustard (Mustargen7), Lewisite, phosgene oxime, and combinations thereof. Preferably, the present invention provides 2-mercaptopyridine-N-oxide compounds for treating, preventing, or inhibiting bis-2-chloroethylsulfide (HD) induced injuries.

2-mercaptopyridine-N-oxide compounds having various substituents on the pyridine ring were designed and synthesized initially as pretreatment antidotes of HD. As shown below in the schematic rational, a thiol 1 with proper pKa is expected to ionize under physiological pH to generate a thiol anion 2.

Rationale

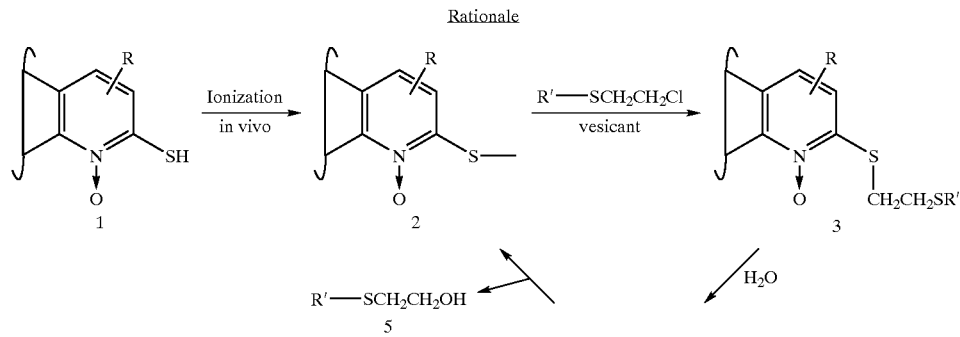

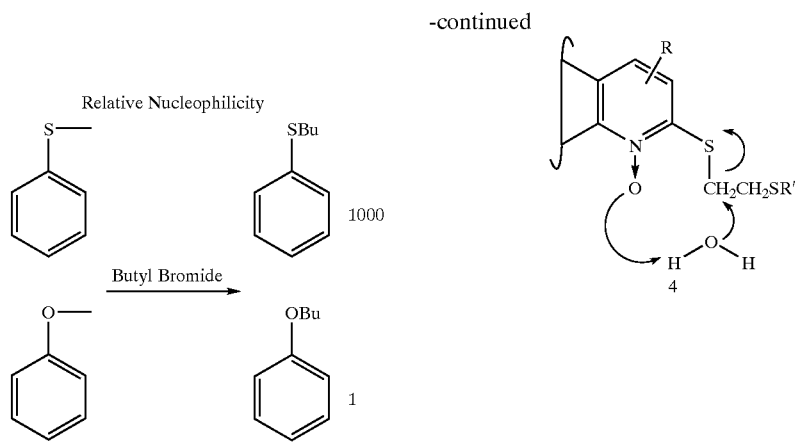

The thiol anion 2 is a potent nucleophile which reacts rapidly with HD to form an inactive adduct 3. The N-oxide function in the inactive adduct 3 is also a strong nucleophile which can either scavenge another molecule of HD or serve as an internal base to catalyze the hydrolysis of the sulfide bond, via transitional intermediate 4, to regenerate the thiol anion 2 and a non-toxic alcohol 5. Therefore, thiols 1 may serve as a catalyst to facilitate the hydrolysis of HD in vivo.

The 2-mercaptopyridine-N-oxide compounds were prepared according to the following scheme.

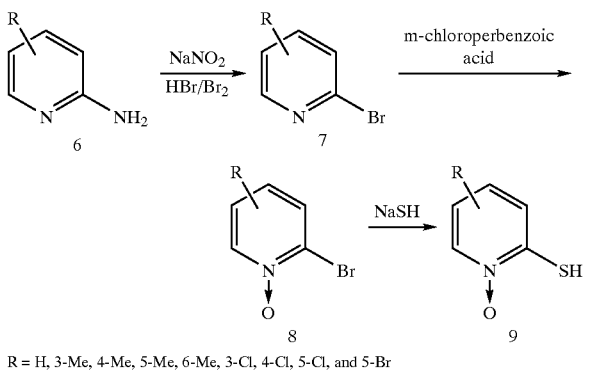

R = H, 3-Me, 4-Me, 5-Me, 6-Me, 3-Cl, 4-Cl, 5-Cl, and 5-Br

Sandmeyer reaction of substituted 2-aminopyridine 6 gave the corresponding 2-bromo-derivatives 7. The N-oxidation of 7 was achieved by treatment of the pyridine ring with m-chloroperbenzoic acid to give the pyridine N-oxide 8. Heating of compound 8 with NaSH aqueous solution gave the final products, substituted 2-mercaptopyridine-N-oxides 9. This procedure was successfully employed to prepare 3-methyl, 4-methyl, 5-methyl-, 5-chloro-, 3-chloro-, 4-chloro-, and 5-bromo-2-mercaptopyridine-N-oxide in yields ranging from about 45% to about 90%.

The antivesicant activities of these 2-mercaptopyridine-N-oxide compounds were assessed by the Mouse Ear Antivesicant Drug Screening Assay Protocol of Institute of Chemical Defense (ICD) as disclosed in Example 1. For the pre-treatment experiments, given concentrations, based on toxicity expectations, limits of solubility, or both, of the test compounds were applied to one side of the mouse ear 15 minutes prior to the HD exposure. For the treatment experiments, various concentrations of the test compounds were applied to one side of the mouse ear at specific times after the HD exposure. The antivesicant activities of the 2-mercaptopyridine-N-oxide compounds were measured by the percentage ear weight reduction of the treated ear versus the untreated control ear weight of the same mouse. The results are shown in Table 1 at Example 1.

Out of the 9 compounds tested, only 3 compounds, 2-mercaptopyridine-N-oxide, 4-methyl-2-mercaptopyridine-N-oxide, and 6-methyl-2-mercaptopyridine-N-oxide, showed significant antivesicant activity. As used herein, "significant antivesicant activity" means greater than about 20% relative ear weight (REW) reduction from the positive HD control ear. 4-Methyl-derivatives showed superior antivesicant activity over the 6-methyl analogs in both 15 minutes pre-exposure (about 57% vs. about 42%) and 10 minutes post-exposure experiments (about 68% vs. about 36%). However, the 6-methyl analog showed better protective efficacy when applied 20 minutes after the HD exposure than the 4-methyl analog (about 25% vs. about 11%), and exhibited significant protective activity even 60 minutes after HD exposure. As shown in the ten minutes post-exposure assay, unsubstituted 2-mercaptopyridine-N-oxide is as active as the 6-methyl-analog, but less active than the 4-methyl-analog. While 4-methyl and 6-methyl substituted 2-mercaptopyridine-N-oxides demonstrated strong antivesicant activity, the 3-methyl and 5-methyl analogs exhibited no statistical significant reduction in relative ear weight (REW) from the positive HD control ear.

The results indicated that the nucleophilicity of pyridine-N-oxide relates to the efficacy of the compound as an antivesicant. Since a methyl group at 4 or 6 position of the pyridine ring is an efficient electron donor which enhanced the nucleophilicity of the N-oxide group and thus potentiated the scavenging activity of the molecule. The chloro or bromo function at 3 or 5 position are electron withdrawing groups which decreased the nucleophilicity of the N-oxide and the SH group, thus failed in the antivesicant tests.

Since the N-oxide function is the reactive site, the methyl group at 6-position of the pyridine ring created a steric hindrance to the reactive site, which may explain why the 6-methyl-2-mercaptopyridine-N-oxide is less active than the 4-methyl-2-mercaptopyridine-N-oxide.

Thus, the present invention relates to compounds comprising the following following Structural Formula A, which comprises 2-mercaptopyridine-N-oxide as a backbone:

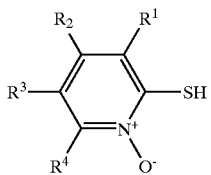

wherein $R^1$, $R^2$, $R^3$, and $R^4$ are each independently H, methyl, halo, trifluoromethyl, nitro, alkyloxy, or acyloxy, preferably, $R^1$, $R^2$, $R^3$, and $R^4$ are each independently H, methyl, methoxy, chloro, fluoro, or bromo, more preferably, $R^1$, $R^2$, $R^3$, and $R^4$ are each independently H, methyl, methoxy, chloro, or bromo. In some preferred embodiments, $R^2$, $R^4$, or both, are a substituent other than H. In some preferred embodiments, two adjacent R group substituents form a ring structure which shares a bond with the pyridine ring to give a compound such as

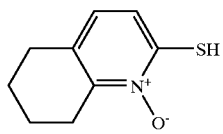

1-Oxy-5,6,7,8-tetrahydro-quinoline-2-thiol,

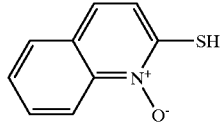

2-mercaptoquinoline-N-oxide,

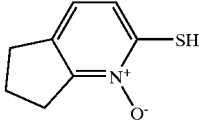

1-Oxy-6, 7-dihydro-5H-[1]pyrindine-2-thiol, and

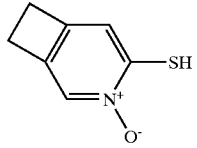

3-Oxy-3-aza-bicyclo[4.2.0]octa-1(6),2,4-triene-4-thiol.

Preferred compounds include 4-methyl and 6-methyl substituted 2-mercaptopyridine-N-oxides. Preferred compounds include:

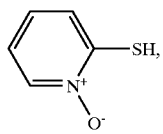

2-mercaptopyridune-N-oxide,

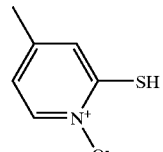

4-methyl-2-mercaptopyridine-N-oxide, and

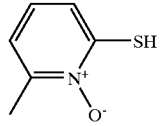

6-methyl-2-mercaptopyridine-N-oxide.

The present invention also provides methods of treating, preventing, or inhibiting an injury induced by a vesicant agent, such as an HD-induced injury, comprising administering at least one compound comprising the following Structural Formula A, which comprises 2-mercaptopyridine-N-oxide as a backbone:

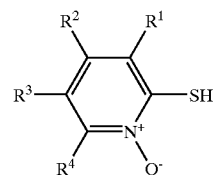

wherein $R^1$, $R^2$, $R^3$, and $R^4$ are each independently H, methyl, halo, trifluoromethyl, nitro, alkyloxy, or acyloxy, preferably, $R^1$, $R^2$, $R^3$, and $R^4$ are each independently H, methyl, methoxy, chloro, fluoro, or bromo, more preferably, $R^1$, $R^2$, $R^3$, and $R^4$ are each independently H, methyl, methoxy, chloro, or bromo. In some preferred embodiments, $R^2$, $R^4$, or both, are a substituent other than H. In some preferred embodiments, two adjacent R group substituents form a ring structure which shares a bond with the pyridine ring. Preferred compounds include 4-methyl and 6-methyl substituted 2-mercaptopyridine-N-oxides.

The present invention also provides a protectant or decontaminant comprising at least one compound comprising the following Structural Formula A, which comprises 2-mercaptopyridine-N-oxide as a backbone:

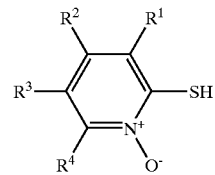

wherein $R^1$, $R^2$, $R^3$, and $R^4$ are each independently H, methyl, halo, trifluoromethyl, nitro, alkyloxy, or acyloxy, preferably, $R^1$, $R^2$, $R^3$, and $R^4$ are each independently H, methyl, methoxy, chloro, fluoro, or bromo, more preferably, $R^1$, $R^2$, $R^3$, and $R^4$ are each independently H, methyl, methoxy, chloro, or bromo. In some preferred embodiments, $R^2$, $R^4$, or both, are a substituent other than H. In some preferred embodiments, two adjacent R group substituents form a ring structure which shares a bond with the pyridine ring. Preferred compounds include 4-methyl and 6-methyl substituted 2-mercaptopyridine-N-oxides. Preferably, the protectant or decontaminant include 4-methyl and 6-methyl substituted 2-mercaptopyridine-N-oxide compounds.

The protectant or decontaminant include clothing, combat gear, protective shelters, weapons, equipment, filters, sponges, foams, sprays, lotions, gases and the like which may be used to protect against or prevent injuries induced by vesicant agents or may be used to decontaminate persons or objects exposed to vesicant agents.

The terms and abbreviations used in the instant disclosure have their normal meanings unless otherwise designated. As used in the present application, the following definitions apply:

As used herein, "antivesicant induced injuries" include those caused by exposure to vesicant agents such as sulfur mustard (bis-2-chloroethylsulfide (HD)), Nitrogen mustard (Mustargen7), Lewisite, phosgene oxime, and combinations thereof. As used herein, "HD-induced injuries" are injuries caused by exposure to HD compounds and combinations comprising HD such as HD Lewisite (HL). Such antivesicant and HD induced injuries include damage to skin, eyes, lungs, including upper and lower airways, and systemic effects such as bone marrow suppression.

As used herein, "antivesicant activity" refers to the activity of a compound which prevents, inhibits or modulates an injury induced by a vesicant agent.

As used herein, "antivesicant" or "antivesicant compound" refers to a compound which exhibits antivesicant activity.

In accordance with a convention used in the art,

is used in structural formulas herein to depict the bond that is the point of attachment of the moiety or substituent to the core or backbone structure. Additionally,

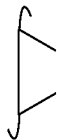

used in the schematic rationale above is used to depict the bonds that are the point of attachment of either two substituents, which may or may not be the same, or a ring structure.

Where chiral carbons are included in chemical structures, unless a particular orientation is depicted, both sterioisomeric forms are intended to be encompassed.

An "alkyl group" is intended to mean a straight or branched chain monovalent radical of saturated and/or unsaturated carbon atoms and hydrogen atoms, such as methyl (Me), ethyl (Et), propyl (Pr), isopropyl (i-Pr), butyl (Bu), isobutyl (i-Bu), t-butyl (t-Bu), ethenyl, pentenyl, butenyl, propenyl, ethynyl, butynyl, propynyl, pentynyl, hexynyl, and the like, which may be unsubstituted (i.e., contain only carbon and hydrogen) or substituted by one or more suitable sustituents as defined below (e.g., one or more halogen, such as F, Cl, Br, or I, with F and Cl being preferred). A "lower alkyl group" is intended to mean an alkyl group having from 1 to 8 carbon atoms in its chain.

A "cycloalkyl group" is intended to mean a non-aromatic monovalent monocyclic, bicyclic, or tricyclic radical comprising 3–14 carbon ring atoms, each of which may be saturated or unsaturated, and which may be unsubstituted or substituted by one or more suitable substituents as defined below, and to which may be fused one or more heterocycloalkyl groups, aryl groups, or heteroaryl groups, which themselves may be unsubstituted or substituted by one or more substituents. Illustrative examples of cycloalkyl groups include the following moieties:

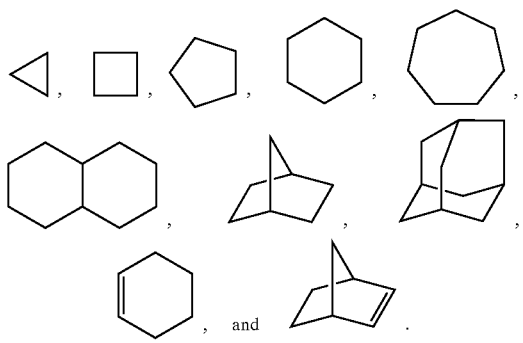

A "heterocycloalkyl group" is intended to mean a non-aromatic monovalent monocyclic, bicyclic, or tricyclic radical, which is saturated or unsaturated, comprising 3–18 ring members, which includes 1–5 heteroatoms selected from nitrogen, oxygen, and sulfur, where the radical is unsubstituted or substituted by one or more suitable substituents as defined below, and to which may be fused one or more cycloalkyl groups, aryl groups, or heteroaryl groups, which themselves may be unsubstituted or substituted by one or more suitable substituents. Illustrative examples of heterocycloalkyl groups include the following moieties:

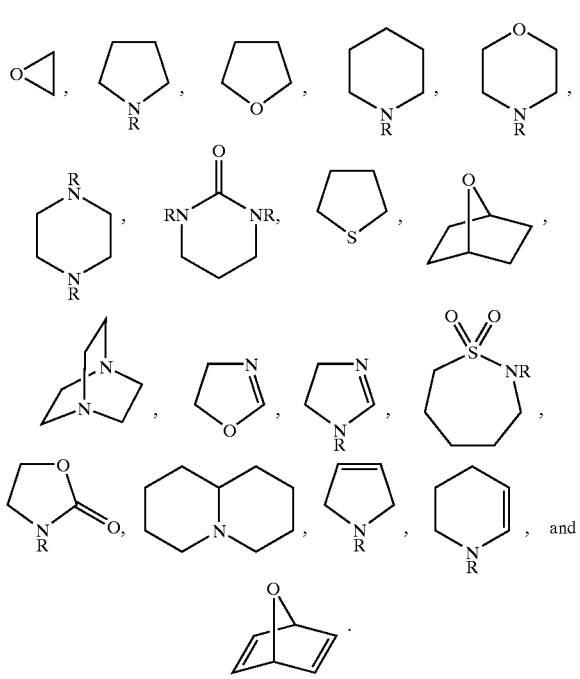

An "aryl group" is intended to mean an aromatic monovalent monocyclic, bicyclic, or tricyclic radical comprising 6, 10, 14, or 18 carbon ring members, which may be unsubstituted or substituted by one or more suitable substituents as defined below, and to which may be fused one or more cycloalkyl groups, heterocycloalkyl groups, or heteroaryl groups, which themselves may be unsubstituted or substituted by one or more suitable substituents. Thus, the term "aryl group" includes a benzyl group (Bzl). Illustrative examples of aryl groups include the following moieties:

A "heteroaryl group" is intended to mean an aromatic monovalent monocyclic, bicyclic, or tricyclic radical comprising 4–18 ring members, including 1–5 heteroatoms selected from nitrogen, oxygen, and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents. Illustrative examples of heteroaryl groups include the following moieties:

A "heterocycle" is intended to mean a heteroaryl or heterocycloalkyl group (each of which, as defined above, are optionally substituted).

The terms "aryl" (Ar) and "heteroaryl" refer to monocyclic and polycyclic unsaturated or aromatic ring structures, with "aryl" referring to those that are carbocycles and "heteroaryl" referring to those that are heterocycles. Examples of aromatic ring structures include phenyl, naphthyl, 1,2,3,4-tetrahydronaphthyl, furyl, thienyl, pyrrolyl, pyridyl, pyridinyl, pyrazolyl, imidazolyl, pyrazinyl, pyridazinyl, 1,2,3-triazinyl, 1,2,4-oxadiazolyl, 1,3,4-oxadiazolyl, 1-H-tetrazol-5-yl, indolyl, quinolinyl, benzofuranyl, benzothiophenyl (thianaphthenyl), and the like.

An "acyl group" is intended to mean a —C(O)—$R^a$ radical, where $R^a$ is a suitable substituent as defined below.

A "thioacyl group" is intended to mean a —C(S)—$R^a$ radical, where $R^a$ is a suitable substituent as defined below.

A "sulfonyl group" is intended to mean a —$SO_2R^a$ radical, where $R^a$ is a suitable substituent as defined below.

A "hydroxy group" is intended to mean the radical —OH.

An "amino group" is intended to mean the radical —$NH_2$.

An "alkylamino group" is intended to mean the radical —$NHR^a$, where $R^a$ is an alkyl group.

A "dialkylamino group" is intended to mean the radical —$NR^aR^b$, where $R^a$ and $R^b$ are each independently an alkyl group.

An "alkoxy group" is intended to mean the radical —$OR^a$, where $R^a$ is an alkyl group. Exemplary alkoxy groups include methoxy, ethoxy, propoxy, and the like.

An "alkoxycarbonyl group" is intended to mean the radical —C(O)$OR^a$, where $R^a$ is an alkyl group.

An "alkylsulfonyl group" is intended to mean the radical —$SO_2R^a$, where $R^a$ is an alkyl group.

An "alkylaminocarbonyl group" is intended to mean the radical —C(O)$NHR^a$, where $R^a$ is an alkyl group.

A "dialkylaminocarbonyl group" is intended to mean the radical —C(O)$NR^aR^b$, where $R^a$ and $R^b$ are each independently an alkyl group.

A "mercapto group" is intended to mean the radical —SH.

An "alkylthio group" is intended to mean the radical —$SR^a$, where $R^a$ is an alkyl group.

A "carboxy group" is intended to mean the radical —C(O)OH.

A "carbamoyl group" is intended to mean the radical —C(O)$NH_2$.

An "aryloxy group" is intended to mean the radical —$OR^c$, where $R^c$ is an aryl group.

A "heteroaryloxy group" is intended to mean the radical —$OR^d$, where $R^d$ is a heteroaryl group.

An "arylthio group" is intended to mean the radical —$SR^c$, where $R^c$ is an aryl group.

A "heteroarylthio group" is intended to mean the radical —$SR^d$, where $R^d$ is a heteroaryl group.

A "leaving group" (Lv) is intended to mean any suitable group that will be displaced by a substitution reaction. One of ordinary skill in the art will know that any conjugate base of a strong acid can act as a leaving group. Illustrative examples of suitable leaving groups include, but are not limited to, —F, —Cl, —Br, alkyl chlorides, alkyl bromides, alkyl iodides, alkyl sulfonates, alkyl benzenesulfonates, alkyl p-toluenesulfonates, alkyl methanesulfonates, triflate, and any groups having a bisulfate, methyl sulfate, or sulfonate ion.

A "protecting group" is intended to refer to groups that protect one or more inherent functional group from premature reaction. Suitable protecting groups may be routinely selected by those skilled in the art in light of the functionality and particular chemistry used to construct the compound. Examples of suitable protecting groups are described, for example, in Greene and Wutz, Protecting Groups in Organic Synthesis, $2^{nd}$ edition, John Wiley and Sons, New York, N.Y. (1991).

The term "suitable organic moiety" is intended to mean any organic moiety recognizable, such as by routine testing, to those skilled in the art as not adversely affecting the inhibitory activity of the inventive compounds. Illustrative examples of suitable organic moieties include, but are not limited to, hydroxyl groups, alkyl groups, oxo groups, cycloalkyl groups, heterocycloalkyl groups, aryl groups, heteroaryl groups, acyl groups, sulfonyl groups, mercapto groups, alkylthio groups, alkoxy groups, carboxy groups, amino groups, alkylamino groups, dialkylamino groups, carbamoyl groups, arylthio groups, heteroarylthio groups, and the like.

In general, the various moieties or functional groups for variables in the formulae may be "optionally substituted" by one or more suitable "substituents". The term "substituent" or "suitable substituent" is intended to mean any suitable substituent that may be recognized or selected, such as through routine testing, by those skilled in the art. Illustrative examples of useful substituents are those found in the exemplary compounds that follow, as well as halogen (chloro, iodo, bromo, or fluoro); $C_{1-6}$-alkyl; $C_{1-6}$-alkenyl; $C_{1-6}$-alkynyl; hydroxyl; $C_{1-6}$ alkoxyl; amino; nitro; thiol; thioether; imine; cyano; amido; phosphonato; phosphine; carboxyl; carbonyl; aminocarbonyl; thiocarbonyl; sulfonyl; sulfonamine; sulfonamide; ketone; aldehyde; ester; oxygen (=O); haloalkyl (e.g., trifluoromethyl); carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); nitro; thiol; thioether, O-lower alkyl; O-aryl, aryl; aryl-lower alkyl; $CO_2CH_3$; $CONH_2$; $OCH_2CONH_2$; $NH_2$; $SO_2NH_2$; $OCHF_2$; $CF_3$; $OCF_3$; and the like. Such moieties may also be optionally substituted by a fused-ring structure or bridge, for example $OCH_2$—O. All of these substituents may optionally be further substituted with a substituent selected from groups such as hydroxy groups, halogens, oxo groups, alkyl groups, acyl groups, sulfonyl groups, mercapto groups, alkylthio groups, alkyloxy groups, cycloalkyl groups, heterocycloalkyl groups, aryl groups, heteroaryl groups, carboxy groups, amino groups, alkylamino groups, dialkylamino groups, carbamoyl groups, aryloxy groups, heteroaryloxy groups, arylthio groups, heteroarylthio groups, and the like.

The term "optionally substituted" is intended to expressly indicate that the specified group is unsubstituted or substituted by one or more suitable substituents, unless the optional substituents are expressly specified, in which case the term indicates that the group is unsubstituted or substituted with the specified substituents. As defined above, various groups may be unsubstituted or substituted (i.e., they are optionally substituted) unless indicated otherwise herein (e.g., by indicating that the specified group is unsubstituted).

It is understood that while a compound of the general structural formulas herein may exhibit the phenomenon of tautomerism, the structural formulas within this specification expressly depict only one of the possible tautomeric forms. It is therefore to be understood that the structural formulas herein are intended to represent any tautomeric form of the depicted compound and is not to be limited merely to a specific compound form depicted by the structural formulas.

It is also understood that the structural formulas are intended to represent any configurational form of the depicted compound and is not to be limited merely to a specific compound form depicted by the structural formulas.

Some of the antivesicants may exist as single stereoisomers (i.e., essentially free of other stereoisomers), racemates, or mixtures of enantiomers, diastereomers, or both. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, if the compounds of the present invention are made synthetically, they are used in a form that is at least 90% optically pure, that is, a form that comprises at least 90% of a single isomer (80% enantiomeric excess (e.e.) or diastereomeric excess (d.e.), more preferably at least 95% (90% e.e. or d.e.), even more preferably at least 97.5% (95% e.e. or d.e.), and most preferably at least 99% (98% e.e. or d.e.).

Additionally, the structural formulas herein are intended to cover, where applicable, solvated as well as unsolvated forms of the compounds. A "solvate" is intended to mean a pharmaceutically acceptable solvate form of a specified compound that retains the biological effectiveness of such compound. Examples of solvates include compounds of the invention in combination with water, isopropanol, ethanol, methanol, dimethyl sulfoxide, ethyl acetate, acetic acid, ethanolamine, or acetone. Also included are miscible formulations of solvate mixtures such as a compound of the invention in combination with an acetone and ethanol mixture. In a preferred embodiment, the solvate includes a compound of the invention in combination with about 20% ethanol and about 80% acetone. Thus, the structural formulas include compounds having the indicated structure, including the hydrated as well as the non-hydrated forms.

As indicated above, the compounds of the invention also include active tautomeric and stereoisomeric forms of the antivesicant compounds of the Structural Formula A, which may be readily obtained using techniques known in the art. For example, optically active (R) and (S) isomers may be prepared via a stereospecific synthesis, e.g., using chiral synthons and chiral reagents, or racemic mixtures may be resolved using conventional techniques.

The antivesicant compounds of the present invention may be prepared using reaction routes, synthesis schemes and techniques available in the art using starting materials that are readily available. The antivesicant compounds of the present invention were made according to the following schemes and methods. However, it should be noted that the antivesicant compounds of the present invention may be made by other methods known in the art.

Substituted 2-Bromopyridine-N-oxide 8 was prepared by the following procedure: 4-methyl-2-bromopyridine (5 g, 29 mmol) was dissolved in 30 ml of chloroform. To the solution was added 80% m-chloroperbenzoic acid (7 g, 35 mmol). The mixture was stirred at room temperature for 4 days, filtered and the precipitate was washed with chloroform. The chloroform filtrate and the washings were combined, and then extracted 3 times with 20% HCl. The HCl extracts were combined and evaporated to dryness under reduced pressure. The residue was recrystallized from EtOH and ether to give 3 grams (about 55%) of white crystals 4-methyl-2-bromopyridine-N-oxide as HCl salts which was converted to free N-oxide before use for the next reaction.

This same procedure was used to prepare 2-bromo-6-methylpyridine-N-oxide (about 53%), 2,5-dibromopyridine-N-oxide (about 50%), 5-methyl-2-bromopyridine-N-oxide (about 90%), 2,3-dichloropyridine-N-oxide (about 45%), 5-chloro-2-bromopyridine-N-oxide (about 55%) and 4-chloro-2-brompyridine-N-oxide (about 65%) from 2-bromo-6-methylpyridine, 2,5-dibromopyridine, 5-methyl-2-bromopyridine, 2,3-dichloropyridine, 5-chloro-2-bromopyridine, and 4-chloro-2-brompyridine, respectively. The identity of these intermediate N-oxides were determined by NMR spectra.

Substituted 2-Mercaptopyridine-N-oxide 9 was prepared by the following procedure: 4-Methyl-2-bromopyridine-N-oxide (1.7 g, 0.01 mol) and NaHS (1.12 g, 0.02 mol) in 10 ml of water was heated on a steam bath for 1.5 hours. The precipitate was removed. The filtrate was acidified with 6N HCl. The product was collected and recrystallized from EtOAc to give light brown color crystals (0.8 g, about 50%), mp about 62 to about 64 C. Anal. (CHNS).

The analogs, 6-methyl-(mp about 54 to about 56 C), 5-bromo-(mp about 135 to about 137 C), 5-methyl-(mp about 107 to about 108 C), 3-chloro- (mp about 108 to about 109 C), 5-chloro-(mp about 133 to about 135 C), and 4-chloro-2-mercaptopyridine (mp about 83 to about 85 C) were prepared by the same procedure starting from the corresponding 2-bromopyridine-N-oxides. All products were identified by NMR and elemental analysis.

Additionally, the compounds of the invention include pharmaceutically acceptable salts, multimeric forms, prodrugs, active metabolites, precursors and salts of such metabolites of the antivesicant compounds of the Structural Formulas described herein.

The term "pharmaceutically acceptable salts" refers to salt forms that are pharmacologically acceptable and substantially non-toxic to the subject being treated with the compound of the invention. Pharmaceutically acceptable salts include conventional acid-addition salts or base-addition salts formed from suitable non-toxic organic or inorganic acids or inorganic bases. Exemplary acid-addition salts include those derived from inorganic acids such as hydrochloric acid, hydrobromic acid, hydroiodic acid, sulfuric acid, sulfamic acid, phosphoric acid, and nitric acid, and those derived from organic acids such as p-toluenesulfonic acid, methanesulfonic acid, ethane-disulfonic acid, isethionic acid, oxalic acid, p-bromophenylsulfonic acid, carbonic acid, succinic acid, citric acid, benzoic acid, 2-acetoxybenzoic acid, acetic acid, phenylacetic acid, propionic acid, glycolic acid, stearic acid, lactic acid, malic acid, tartaric acid, ascorbic acid, maleic acid, hydroxymaleic acid, glutamic acid, salicylic acid, sulfanilic acid, and fumaric acid. Exemplary base-addition salts include those derived from ammonium hydroxides (e.g., a quaternary ammonium hydroxide such as tetramethylammonium hydroxide), those derived from inorganic bases such as alkali or alkaline earth-metal (e.g., sodium, potassium, lithium, calcium, or magnesium) hydroxides, and those derived from non-toxic organic bases such as basic amino acids.

The term "multimer" refers to multivalent or multimeric forms of active forms of the compounds of the invention. Such "multimers" may be made by linking or placing multiple copies of an active compound in close proximity to each other, e.g., using a scaffolding provided by a carrier moiety. Multimers of various dimensions (i.e., bearing varying numbers of copies of an active compound) may be tested to arrive at a multimer of optimum size with respect to receptor binding. Provision of such multivalent forms of active receptor-binding compounds with optimal spacing between the receptor-binding moieties may enhance receptor binding. See, for example, Lee et al., (1984) Biochem. 23:4255. The artisan may control the multivalency and spacing by selection of a suitable carrier moiety or linker units. Useful moieties include molecular supports comprising a multiplicity of functional groups that can be reacted with functional groups associated with the active compounds of the invention. A variety of carrier moieties may be used to build highly active multimers, including proteins such as BSA (bovine serum albumin) or HSA, peptides such as pentapeptides, decapeptides, pentadecapeptides, and the like, as well as non-biological compounds selected for their beneficial effects on absorbability, transport, and persistence within the target organism. Functional groups on the carrier moiety, such as amino, sulfhydryl, hydroxyl, and alkylamino groups, may be selected to obtain stable linkages to the compounds of the invention, optimal spacing between the immobilized compounds, and optimal biological properties.

"A pharmaceutically acceptable prodrug" is a compound that may be converted under physiological conditions or by solvolysis to the specified compound or to a pharmaceutically acceptable salt of such compound. "A pharmaceutically active metabolite" is intended to mean a pharmacologically active product produced through metabolism in the body of a specified compound or salt thereof. Prodrugs and active metabolites of a compound may be identified using routine techniques known in the art. See, e.g., Bertolini, G. et al., (1997) J. Med. Chem. 40:2011–2016; Shan, D. et al., *J. Pharm. Sci.,* 86(7):765–767; Bagshawe K., (1995) Drug Dev. Res. 34:220–230; Bodor, N., (1984) Advances in Drug Res. 13:224–331; Bundgaard, H., *Design of Prodrugs* (Elsevier Press, 1985); and Larsen, I. K., *Design and Application of Prodrugs,* Drug Design and Development (Krogsgaard-Larsen et al., eds., Harwood Academic Publishers, 1991).

If the antivesicant compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyrvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the antivesicant compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from basic amino acids, such as lysine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium. Preferred amines and salts thereof are those that are clinically acceptable, i.e. not too toxic in the subject being treated.

In the case of compounds that are solids, it is understood by those skilled in the art that the inventive compounds and salts may exist in different crystal or polymorphic forms, all of which are intended to be within the scope of the present invention and specified structural formulas.

The antivesicant activity of the antivesicant compounds of the present invention may be measured by any of the methods available to those skilled in the art, including in vitro and in vivo assays. Examples of suitable assays for activity measurements are provided herein. Properties of the antivesicant compounds may be assessed, for example, by using one or more of the assays set out in the Examples below. Other pharmacological methods may also be used to determine the efficacy of the compounds as antivesicant compounds.

The antivesicant compounds in accordance with the present invention are useful in the treatment of antivesicant induced injuries, preferably HD-induced injuries and the like. Such antivesicant and HD induced injuries include cutaneous, ocular and pulmonary injuries such as damage to skin, eyes, lungs, including upper and lower airways, and systemic effects such as bone marrow suppression.

The antivesicant compounds of the present invention may be used in combination with or as a substitution for treatments of the above conditions. For example, the antivesicant compounds may also be used alone or in combination with a supplementary active compound such as anti-inflammatory and anti-protease drugs and the like to treat, prevent or inhibit antivesicant induced injuries such as HD-induced injuries associated with exposure to HD compounds and derivatives.

An antivesicant compound of the present invention may be administered in a therapeutically effective amount to a mammal such as a human. A therapeutically effective amount may be readily determined by standard methods known in the art. As used herein, a "therapeutically effective amount" of an antivesicant compound of the present invention is an amount which prevents, inhibits, suppresses or reduces the amount of injury or damage caused by exposure to a vesicant agent, such as an HD compound or derivative thereof, in a subject as compared to a control.

As defined herein, a therapeutically effective amount of a compound of the present invention may be readily determined by one of ordinary skill by routine methods known in the art. Preferred topical concentrations include about 0.1% to about 10% in a formulated salve. The skilled artisan will appreciate that certain factors may influence the dosage required to effectively treat a subject, including but not limited to the severity of the disease or disorder, previous treatments, the general health and/or age of the subject, and other diseases present.

Moreover, treatment of a subject with a therapeutically effective amount of the antivesicant compound preferably includes a single treatment, but can include a series of treatments. For example, a subject may be treated with an antivesicant compound of the invention at least once. However, the subject may treated with the antivesicant compound from about one time per week to about several times daily for a given treatment period. The length of the treatment period will depend on a variety of factors such as the length of exposure to the vesicant agent, the severity of the injury, the predisposition of exposure to a vesicant compound, or a combination thereof. It will also be appreciated that the effective dosage of the compound used for treatment may increase or decrease over the course of a particular treatment. Changes in dosage may result and become apparent by standard diagnostic assays known in the art. In some instances chronic administration may be required. The antivesicant compound may be administered before, during, after, or a combination thereof exposure to a vesicant agent.

The pharmaceutical compositions of the invention may be prepared in a unit-dosage form appropriate for the desired mode of administration. The compositions of the present invention may be administered for therapy by any suitable route including oral, rectal, nasal, topical (including buccal and sublingual), vaginal and parenteral (including subcutaneous, intramuscular, intravenous and intradermal). It will be appreciated that the preferred route will vary with the condition and age of the recipient, the nature of the condition to be treated, and the chosen active compound.

It will be appreciated that the actual dosages of the compounds used in the compositions of this invention will vary according to the particular complex being used, the particular composition formulated, the mode of administration, and the particular site, host, and disease being treated. Optimal dosages for a given set of conditions may be ascertained by those skilled in the art using conventional dosage-determination tests in view of the experimental data for a given antivesicant compound. Administration of prodrugs may be dosed at weight levels that are chemically equivalent to the weight levels of the fully active forms.

The antivesicant compounds of the invention can be incorporated into pharmaceutical compositions suitable for administration. Pharmaceutical compositions of this invention comprise a therapeutically effective amount of an antivesicant compound having the Structural Formula A, and an inert, pharmaceutically acceptable carrier or diluent. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like. The use of such media and agents for pharmaceutically active substances is well known in the art.

Except insofar as any conventional media or agent is incompatible with the active compound, use thereof in the compositions is contemplated. Supplementary active compounds can also be incorporated into the compositions. Supplementary active compounds include anti-inflammatory and anti-protease drugs and other compounds commonly used to treat injuries induced by exposure to vesicant agents.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution in an ampoule or vial or non-aqueous liquid suspension.

To obtain a stable water-soluble dose form, a pharmaceutically acceptable salt of an inventive agent is dissolved in an aqueous solution of an organic or inorganic acid, such as 0.3M solution of succinic acid or citric acid. If a soluble salt form is not available, the agent may be dissolved in a suitable co-solvent or combinations of co-solvents. Examples of suitable co-solvents include, but are not limited to, alcohol, propylene glycol, polyethylene glycol 300, polysorbate 80, glycerin and the like in concentrations ranging from 0–60% of the total volume. In an exemplary embodiment, the antivesicant compound of the present invention is dissolved in DMSO and diluted with water.

The composition may also be in the form of a solution of a salt form of the active ingredient in an appropriate aqueous vehicle such as water or isotonic saline or dextrose solution.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations which can be used pharmaceutically.

Proper formulation is dependent upon the route of administration chosen. For injection, the agents of the invention may be formulated into aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (compound), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally comprise gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compounds and agents.

Pharmaceutical preparations which can be used orally include push-fit capsules made of gelatin, as well as soft, sealed capsules made of gelatin and a plasticizer, such as glycerol or sorbitol. The push-fit capsules can comprise the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can comprise any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Preferred formulations for oral formulations include microcrystalline tablets, gelatin capsules, or the like.

For administration intranasally or by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated comprising a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may comprise formulatory agents such as suspending, stabilizing and/or dispersing agents.

Pharmaceutical compositions suitable for injectable use include sterile aqueous solutions (where water soluble) or dispersions and sterile powders for the extemporaneous preparation of sterile injectable solutions or dispersion. Aqueous injection suspensions may comprise substances which increase the viscosity of the suspension, such as sodium carboxymethyl cellulose, sorbitol, or dextran. Optionally, the suspension may also comprise suitable stabilizers or agents which increase the solubility of the compounds to allow for the preparation of highly concentrated solutions. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes.

For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium comprising, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating a therapeutically effective amount of a compound of the invention in an appropriate solvent with one or a combination of ingredients enumerated above, as required, followed by filtered sterilization. Generally, dispersions are prepared by incorporating the antivesicant compound into a sterile vehicle which comprises a basic dispersion medium and the required other ingredients from those enumerated above. In the case of sterile powders for the preparation of sterile injectable solutions, the preferred methods of preparation are vacuum drying and freeze-drying which yields a powder of the active compound plus any additional desired ingredient from a previously sterile-filtered solution thereof.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, foams, powders, sprays, aerosols or creams as generally known in the art.

For example, for topical formulations, pharmaceutically acceptable excipients may comprise solvents, emollients, humectants, preservatives, emulsifiers, and pH agents. Suitable solvents include ethanol, acetone, glycols, polyurethanes, and others known in the art. Suitable emollients include petrolatum, mineral oil, propylene glycol dicaprylate, lower fatty acid esters, lower alkyl ethers of propylene glycol, cetyl alcohol, cetostearyl alcohol, stearyl alcohol, stearic acid, wax, and others known in the art. Suitable humectants include glycerin, sorbitol, and others known in the art. Suitable emulsifiers include glyceryl monostearate, glyceryl monoleate, stearic acid, polyoxyethylene cetyl ether, polyoxyethylene cetostearyl ether, polyoxyethylene stearyl ether, polyethylene glycol stearate, propylene glycol stearate, and others known in the art. Suitable pH agents include hydrochloric acid, phosphoric acid, diethanolamine, triethanolamine, sodium hydroxide, monobasic sodium phosphate, dibasic sodium phosphate, and others known in the art. Suitable preservatives include benzyl alcohol, sodium benzoate, parabens, and others known in the art.

For administration to the eye, the compound of the invention is delivered in a pharmaceutically acceptable ophthalmic vehicle such that the compound is maintained in contact with the ocular surface for a sufficient time period to allow the compound to penetrate the corneal and internal regions of the eye, including, for example, the anterior chamber, posterior chamber, vitreous body, aqueous humor, vitreous humor, cornea, iris/cilary, lens, choroid/retina and selera. The pharmaceutically acceptable ophthalmic vehicle may be an ointment, vegetable oil, or an encapsulating material. A compound of the invention may also be injected directly into the vitreous and aqueous humor.

Alternatively, the active ingredient may be in powder form for constitution with a suitable vehicle, e.g., sterile pyrogen-free water, before use. The compounds may also be formulated in rectal compositions such as suppositories or retention enemas, e.g., comprising conventional suppository bases such as cocoa butter or other glycerides.

In addition to the formulations described above, the compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

A pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) comprises VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied, for example: other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers comprising the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter ions. Pharmaceutically compatible salts may be formed with many acids, including hydrochloric, sulfuric, acetic, lactic, tartaric, malic, succinic, etc. Salts tend to be more soluble in aqueous or other protonic solvents than are the corresponding free-base forms.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit comprising a predetermined quantity of active compound calculated to produce the desired therapeutic effect in association with the required pharmaceutical carrier.

The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The following examples are intended to illustrate but not to limit the invention.

EXAMPLE 1

Mouse Ear Antivesicant Drug Screening Assay

The effect of topical application of HD to the medial aspect of the right ear was evaluated in albino male mice (CD-1 Strain, Charles Rivers Laboratory, Kingston, N.Y.) weighing about 25 to about 35 grams. Mice were weighed, marked for identification and anesthetized with a combination of ketamine (60 mg/kg) and xylazine (12 mg/kg) given as an intraperitoneal injection. In a fume hood, 5 μl (0.16 mg) of a 195 mM solution of neat (undiluted) HD (d=1.27 g/ml; MW 159; purity 97.5%) in methylene chloride was applied to the medial surface of the right ear of each mouse using a digital microliter positive displacement pipette. This volume of HD allowed even distribution of the vesicant agent over the entire medial surface of the ear.

Mice were returned to polycarbonate cages for recovery, observation and treatment. Each cage was covered with a plastic backed paper diaper and warmed using a circulating water heating pad placed under the container. All animals were housed in the hood until euthanized in a halothane-filled chamber. The animals were euthanized 24 hours after exposure. Immediately after euthanasia, full thickness circular 8 mm punched specimens were taken from the center of each ear, placed into tarred 1.5 ml microfuge vials, and weighed to the nearest 0.1 mg on an analytical balance to determine tissue wet weight. This tissue wet-weight was used to determine an index of edema (relative ear weight, REW), which was used as the primary quantitative response to tissue injury.

$$REW = \frac{(\text{exposed ear} - \text{control ear})}{\text{control ear}} \times 100$$

Each 8 mm punched biopsy specimen was then divided. One half of the tissue was placed into a vial comprising 10% neutral buffered formalin (NBF) for histopathological evaluation while the remaining half was snap frozen in liquid nitrogen for immunohistochemistry or for later processing in biochemical or molecular biology assays.

For each experiment, 10 mice per treatment group were used. The right ears of all groups of mice were exposed to HD liquid. Treatment groups were administered candidate antivesicant drugs as a pre-treatment (15 minutes before HD exposure) or post-treatment. Each mouse acted as its own control since the left ear was only treated with HD vehicle (MeCl$_2$). In addition, 10 mice per experiment were used as HD positive controls. Previous in-house studies using a one-way analysis of variance (ANOVA) revealed no significant histopathologic differences in the effects of a methylene chloride (HD vehicle) treated ear and a control ear. Therefore, methylene chloride was only used on control ears that were used for biochemical or molecular biology assays.

After fixation in neutral buffered formalin (NBF), tissues were embedded in paraffin then sectioned and stained with hematoxylin/eosin (H&E) for microscopic evaluation. Histopathologic endpoints, subepidermal blister and epidermal necrosis, as described below, were given severity scores. See also Casillas, R. P., et al. (1997) Tox. Meth. 7:381–397 and Monteiro-Riviere, N. A., et al. (1999) J. Appl. Toxicol. 19, 313–328, both of which are herein incorporated by reference.

(a). Subepidermal blister (SEB; epidermal-dermal separation) and opposite side (contralateral) subepidermal blister (CSEB; unexposed outer surface). A SEB is any defect or discontinuity involving detachment of basal cells from the basement membrane.

(b). Epidermal necrosis (EN; exposed inner ear surface) and opposite side (contralateral) epidermal necrosis (CEN; unexposed outer ear surface). Epidermal necrosis denotes cellular death in the epithelium.

The severity scores were as follows: 0=no lesion or change; 1=change in less than 5% of the entire tissue section; 2=change is present in 10%–40% of the entire tissue section; 3=change is present in 50%–80% of the entire tissue section; 4=change is present in greater than 90% of the entire tissue section. Scores were reported as the mean of each group.

The results are shown in Table 1 as follows:

TABLE 1

| Compound Name | Total Dose | Time of Application (before or after exposure) | % REW reduction | % SEB reduction | % EN reduction | % CEN reduction |
|---|---|---|---|---|---|---|
| MPNO | 0.6 mg | −15 minute | 35.96 | 50.00 | 5.88 | 65.63 |
| | 0.6 mg | +10 minute | 59.71 | 100 | 54.55 | 66.67 |
| | 0.6 mg | +10 minute | 36.12 | 88.89 | 30.77 | 77.14 |
| | 0.6 mg | +20 minute | 16.37 | 77.78 | 7.69 | 48.57 |
| | 0.15 mg | −15 minute | 27.24 | 75.00 | 10.53 | 44.12 |
| | 0.3 mg | −15 minute | 38.20 | 75.00 | 31.58 | 55.88 |
| | 0.6 mg | −15 minute | 41.65 | 50.00 | 26.32 | 50.00 |
| | 1.2 mg | −15 minute | 47.68 | 75.00 | 31.58 | 91.18 |
| | 2.4 mg | −15 minute | 69.42 | 100 | 68.42 | 94.12 |
| | 0.15 mg | +10 minute | 7.02 | 25.00 | 2.78 | 46.67 |
| | 0.3 mg | +10 minute | 3.29 | 100.00 | −8.33 | 53.33 |
| | 0.6 mg | +10 minute | 11.27 | 50.00 | 8.33 | 46.67 |
| | 1.2 mg | +10 minute | 26.24 | 50.00 | 2.78 | 50.00 |
| | 2.4 mg | +10 minute | 24.71 | 0.00 | −5.56 | 53.33 |
| 4-Me-MPNO | 0.6 mg | −15 minute | 57.05 | 25.00 | 14.71 | 93.75 |
| | 0.6 mg | +10 minute | 17.29 | 44.44 | 5.56 | 65.81 |
| | 0.6 mg | +10 minute | 67.78 | 100.00 | 57.58 | 85.19 |
| | 0.6 mg | +20 minute | 10.64 | 50.00 | 2.50 | 28.21 |
| | 0.15 mg | −15 minute | 25.37 | 0.00 | 10.81 | 71.88 |
| | 0.3 mg | −15 minute | 38.95 | 60.00 | 13.51 | 68.75 |
| | 0.6 mg | −15 minute | 57.20 | 100.00 | 29.73 | 71.88 |
| | 1.2 mg | −15 minute | 48.70 | 60.00 | 27.03 | 75.00 |
| | 2.4 mg | −15 minute | 69.11 | 80.00 | 48.65 | 84.38 |
| | 0.15 mg | +10 minute | 34.01 | 57.14 | 2.56 | 60.00 |
| | 0.3 mg | +10 minute | 41.93 | 57.14 | 10.26 | 68.57 |
| | 0.6 mg | +10 minute | 40.36 | 71.43 | 7.69 | 65.71 |
| | 1.2 mg | +10 minute | 30.99 | 71.43 | 7.69 | 71.43 |
| | 2.4 mg | +10 minute | 30.40 | 85.71 | 20.51 | 68.57 |
| 6-Me-MPNO | 0.6 mg | −15 minute | 42.15 | 50.00 | 17.65 | 56.25 |
| | 0.6 mg | +10 minute | 27.61 | 50.00 | 24.24 | 59.26 |
| | 0.6 mg | +10 minute | 35.74 | 61.43 | 3.33 | 24.40 |
| | 0.6 mg | +20 minute | 25.19 | 87.14 | 3.33 | 31.60 |
| | 0.6 mg | +60 minute | 22.17 | 74.29 | 3.33 | 17.20 |
| | 0.15 mg | −15 minute | 19.81 | −25.00 | 7.89 | 41.18 |
| | 0.3 mg | −15 minute | 21.62 | −25.00 | 5.26 | 52.94 |
| | 0.6 mg | −15 minute | 14.63 | −50.00 | 0.00 | 35.29 |
| | 1.2 mg | −15 minute | 47.80 | 50.00 | 0.00 | 67.65 |
| | 2.4 mg | −15 minute | 40.13 | 75.00 | 23.68 | 64.71 |
| | 0.15 mg | +10 minute | 0.97 | 0.00 | −8.57 | 17.86 |
| | 0.3 mg | +10 minute | 10.95 | 0.00 | −5.71 | 32.14 |
| | 0.6 mg | +10 minute | 19.47 | 50.00 | 5.71 | 35.71 |
| | 1.2 mg | +10 minute | 19.98 | 0.00 | 2.86 | 17.86 |
| | 2.4 mg | +10 minute | 10.39 | 25.00 | −5.71 | 57.14 |
| 4,6-di-Me-MPNO | 0.6 mg | −15 minute | 36.85 | n/t | n/t | n/t |
| 5-Br-MPNO | 0.6 mg | −15 minute | 15.61 | n/t | n/t | n/t |
| 5-Cl-MPNO | 0.6 mg | −15 minute | 5.32 | n/t | n/t | n/t |
| 3-Cl-MPNO | 0.6 mg | −15 minute | 18.31 | n/t | n/t | n/t |

MPNO = 2-mercaptopyridine-N-oxide;
Me = Methyl;
% REW = % Reduction in mouse EarWeight;
SEB % reduction = % reduction in severity of Sub-epidermal Blister;
EN % reduction = % reduction in severity of Epidermal Necrosis;
CEN % reduction = % reduction in severity of Contralateral Epidermal Necrosis, as compared with the untreated control mouse year.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

We claim:

1. A method of treating, preventing, or inhibiting an injury induced by a vesicant agent comprising administering at least one compound selected from the group consisting of 2-mercaptopyridine-N-oxide and pharmaceutically acceptable salts thereof, 4-methyl-2-mercaptopyridine-N-oxide and pharmaceutically acceptable salts thereof, and 6-methyl-2-mercaptopyridine-N-oxide and pharmaceutically acceptable salts thereof to a subject in need thereof.

2. The method of claim 1, wherein the compound is administered before exposure to the vesicant agent.

3. The method of claim 1, wherein the compound is administered during exposure to the vesicant agent.

4. The method of claim 1, wherein the compound is administered after exposure to the vesicant agent.

5. The method of claim 1, wherein the injury is an HD-induced injury.

6. The method of claim 1, wherein the compound is administered topically.

7. The method of claim 1, wherein the compound is administered systemically.

8. The method of claim 1, wherein the compound is in the form of a pharmaceutical composition.

9. The method of claim 1, further comprising administering a compound selected from the group consisting of 2-mercaptopyridine-N-oxide and pharmaceutically acceptable salts thereof, 4-methyl-2-mercaptopyridine-N-oxide and pharmaceutically acceptable salts thereof, and 6-methyl-2-mercaptopyridine-N-oxide and pharmaceutically acceptable salts thereof to the subject in need thereof.

* * * * *